United States Patent
Henning et al.

(10) Patent No.: US 10,266,658 B2
(45) Date of Patent: Apr. 23, 2019

(54) OEM TEXTILE FINISHING COMPOSITIONS

(71) Applicants: EVONIK DEGUSSA GMBH, Essen (DE); EVONIK SPECIALTY CHEMICALS (SHANGHAI) CO. LTD., Shanghai (CN)

(72) Inventors: Frauke Henning, Essen (DE); Jörg Peggau, Essen (DE); Andrea Lohse, Bottrop (DE); Ulrike Mahring, Essen (DE); Fuming Chen, Shanghai (CN)

(73) Assignee: EVONIK DEGUSSA GMBH, Essen (DE)

( * ) Notice: Subject to any disclaimer, the term of this patent is extended or adjusted under 35 U.S.C. 154(b) by 52 days.

(21) Appl. No.: 15/546,142

(22) PCT Filed: Feb. 28, 2015

(86) PCT No.: PCT/CN2015/073404
§ 371 (c)(1),
(2) Date: Jul. 25, 2017

(87) PCT Pub. No.: WO2016/134538
PCT Pub. Date: Sep. 1, 2016

(65) Prior Publication Data
US 2018/0009954 A1    Jan. 11, 2018

(51) Int. Cl.
*C08G 77/54*    (2006.01)
*A61Q 5/12*    (2006.01)
(Continued)

(52) U.S. Cl.
CPC ............ *C08G 77/54* (2013.01); *A61C 5/12* (2013.01); *A61K 8/898* (2013.01); *C08G 81/00* (2013.01);
(Continued)

(58) Field of Classification Search
None
See application file for complete search history.

(56) References Cited

U.S. PATENT DOCUMENTS

| 4,659,545 A | 4/1987 | Ferrari |
| 4,891,166 A * | 1/1990 | Schaefer ............... A61K 8/898 554/39 |

(Continued)

FOREIGN PATENT DOCUMENTS

| CN | 1509305 A | 6/2004 |
| CN | 1657687 A * | 8/2005 |

(Continued)

OTHER PUBLICATIONS

International Search Report dated Nov. 18, 2015 in PCT/CN2015/073404 (3 pages).

(Continued)

*Primary Examiner* — Peter A Salamon
(74) *Attorney, Agent, or Firm* — Philip P. McCann; Nexsen Pruet, PLLC

(57) ABSTRACT

Crosslinked aminosiloxanes obtainable by reaction of identical or different aminosiloxanes with identical or different epoxide components which are water-soluble hydrocarbons, the hydrocarbons comprising oxygen as well as carbon, and optionally further elements selected from nitrogen, sulphur and phosphorus, the hydrocarbon having on average more than one terminal epoxy group, the epoxy group being a carbooxirane radical, and, further, not more than 50% of all the amino groups having undergone reaction with an epoxide group.

16 Claims, 1 Drawing Sheet

(51) Int. Cl.
*C08G 81/00* (2006.01)
*A61C 5/12* (2006.01)
*D06M 15/643* (2006.01)
*D06M 15/65* (2006.01)
*C08L 83/14* (2006.01)
*C08J 3/24* (2006.01)
*A61K 8/898* (2006.01)
*D06M 101/32* (2006.01)

(52) U.S. Cl.
CPC ............... *C08J 3/24* (2013.01); *C08L 83/14* (2013.01); *D06M 15/6436* (2013.01); *D06M 15/652* (2013.01); *D06M 2101/32* (2013.01); *D06M 2200/50* (2013.01)

(56) References Cited

U.S. PATENT DOCUMENTS

| | | | |
|---|---|---|---|
| 5,807,956 A * | 9/1998 | Czech | A61K 8/898 424/70.122 |
| 7,153,922 B2 | 12/2006 | Hohberg et al. | |
| 7,652,120 B2 | 1/2010 | Danner et al. | |
| 8,621,256 B2 | 12/2013 | Minami | |
| 8,653,320 B2 | 2/2014 | Furno et al. | |
| 8,949,640 B2 | 2/2015 | Minami | |
| 8,957,009 B2 | 2/2015 | Schubert et al. | |
| 9,695,202 B2 * | 7/2017 | Henning | C07F 7/1804 |
| 2004/0225099 A1 * | 11/2004 | Hohberg | A61K 8/898 528/25 |
| 2005/0053570 A1 * | 3/2005 | Hirai | A61K 8/894 424/70.122 |
| 2012/0308494 A1 * | 12/2012 | Schubert | A61K 8/898 424/59 |
| 2013/0040875 A1 * | 2/2013 | Henning | C08G 77/08 510/527 |
| 2018/0009954 A1 | 1/2018 | Henning et al. | |

FOREIGN PATENT DOCUMENTS

| | | |
|---|---|---|
| CN | 1657687 A | 8/2005 |
| CN | 102199295 A | 9/2011 |
| CN | 102585229 A | 7/2012 |
| CN | 102725031 A | 10/2012 |
| DE | 102004012877 A1 | 7/2005 |
| DE | 102011110100 A1 | 2/2013 |
| EP | 0294642 A2 | 12/1988 |
| EP | 1477513 A1 | 11/2004 |
| EP | 2557107 A1 | 2/2013 |
| KR | 2009130695 | 12/2009 |
| WO | 2009061362 A2 | 5/2009 |

OTHER PUBLICATIONS

Peggau et al., U.S. Appl. No. 15/509,685, filed Mar. 8, 2017.
Written Opinion dated Nov. 18, 2015 in PCT/CN2015/073404 (4 pages).

* cited by examiner

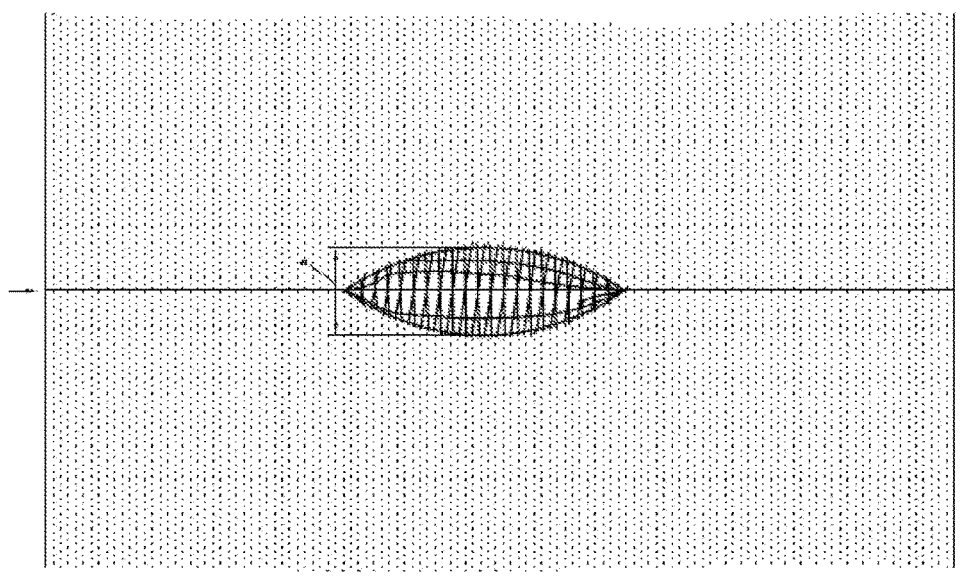

OEM TEXTILE FINISHING COMPOSITIONS

This application is a national stage application under 35 U.S.C. § 371 of International Application No. PCT/CN2015/073404 filed 28 Feb. 2015, the disclosure of which is expressly incorporated herein by reference.

FIELD

Crosslinked aminosiloxanes obtainable by reaction of identical or different aminosiloxanes with identical or different epoxide components which are water-soluble hydrocarbons, the hydrocarbons comprising oxygen as well as carbon, and optionally further elements selected from nitrogen, sulphur and phosphorus, the hydrocarbon having on average more than one terminal epoxy group, the epoxy group being a carbooxirane radical, and, further, not more than 50% of all the amino groups having undergone reaction with an epoxide group.

BACKGROUND

Hydrophobic fabrics of polyester or polyamide, for example, or else blend fabrics with cotton, in the course of their production, are post-treated in aqueous liquor with hydrophilizing agents and conditioning agents, in order to finish the fabric such that it is pervious to damp air—that is "breathable"—and retains its shape, in conjunction with a good soft hand.

Reactive prepolymers, such as amino-functional and epoxy-functional polyether siloxanes, for example, can be cured with one another on the fiber to form high molecular mass coatings, as described in U.S. Pat. No. 4,659,545 A1, for example. Efficient, uniform application of the hydrophilic reactive polymers into the fiber, and quantitative reaction of the components are difficult to control. Many of these amino silicone emulsions lack temperature stability, and the resulting hydrophilization may therefore be uneven. This unevenness is manifested on the textile, after the subsequent dyeing operation, by phenomena such as oil spotting, for example, leading to these goods being rejected.

Frequently used are emulsions comprising aminosiloxanes or silicone quats as their active component (Roulette: Handbuch Textilveredelung [Textile Finishing Handbook], Volume II, 14th edn. 2003, 304 ff). The emulsifier used for the emulsification, generally a fatty alcohol ethoxylate, likewise goes onto the textile surface and partly displaces the active component or prevents it from anchoring to the fiber, meaning that conditioning is not efficient. Leaching of the emulsifier and of the inadequately anchored active component during the first few times the textile is laundered is very soon unmistakeable, since the garment suffers impaired tactility. Moreover, the additional use of emulsifiers leads to increased migration into the fibers. The result of this is not only a loss of active substance but also an increased tendency for slippage of the fibers relative to one another. This is manifested in reduced dimensional stability on the part of the completed textile.

When sufficiently hydrophilic, more hydrophilic siloxane-polymer copolymers containing amino groups or cationic groups, such as, for example, the linear ABn block copolymers described in US 2012-0308494, CN 102199295, KR 2009130695 and U.S. Pat. No. 5,807,956, or pendant or terminal aminosiloxanes functionalized with monoepoxy polyethers and described by way of example in US 2005-0053570 or EP 1477513 A1 (US 2004-0225099), can be formulated without emulsifier. Nevertheless, because of their increased hydrophilicity, they are not so good at depositing on the textile. The anchoring on the textile surface is primarily adsorptive and less permanent, since the secondary and tertiary amino groups are sterically hindered and insufficiently reactive for interaction with the polyester groups. High molar masses are required, which go hand in hand with high viscosities and greater formulation difficulties in order to reduce inevitable leaching to an acceptable degree.

SiOC-aminopolyethersiloxanes are out of the question on account of instability to hydrolysis, undergoing breakdown even in the liquor before they deposit on the textile, and being decomposed more quickly than SiC-functional siloxanes, at the alkaline wash stage, if not earlier (cf. WO 200961362).

Possessing a much more strongly pronounced silicone character, in contrast, are cationic silicones, of the kind described in EP 0 294 642 (U.S. Pat. No. 4,891,166). EP 0 294 642 describes structures where the quaternary functions are bonded terminally to a siloxane segment. When a textile is treated with such compounds, it does indeed acquire a good soft hand, but the low substantivity of the siloxane means that it is easily removable from the corresponding textile again, as a result of laundering procedures, for example. Furthermore, compounds of this kind can be adequately fixed usually only on natural fibers. In contrast to the household fabric softener, however, it is desirable, for industrial OEM textile finishing, for the siloxane to remain on the textile even after laundering and hence for the soft hand to be maintained.

All of the prior-art finishing compositions for hydrophilization have the disadvantage of an inadequate dimensional stability.

SUMMARY

It was an object of the present invention, therefore, to provide hydrophilizing agents which avoid one or more disadvantages of the prior art.

Surprisingly it has been found that aminosiloxanes crosslinked with epoxy components that have more than one epoxy group bring about high dimensional stability and at the same time effective hydrophilization.

DETAILED DESCRIPTION

The present invention provides crosslinked aminosiloxanes obtainable by reaction of identical or different amine-substituted siloxanes with identical or different epoxide components which are water-soluble hydrocarbons, the hydrocarbons comprising oxygen as well as carbon, and optionally further elements selected from nitrogen, sulphur and phosphorus, the hydrocarbon having on average more than one terminal epoxy group, the epoxy group being a carbooxirane radical, and, further, not more than 50% of all the amino groups having undergone reaction with an epoxide group.

Water-soluble in the context of the invention is understood to mean a hydrocarbon having a solubility of at least 1 g/l, preferably at least 2 g/l, 5 g/l, 10 g/l and especially preferably of at least 15 g/l water at a temperature of 20° C. The upper solubility limit is preferably up to and including 500 g/l, more preferably 300 g/l, 200 g/l and especially preferably up to and including 100 g/l water at 20° C. Determining the water-solubility is comprehensible to the skilled person, who determines it preferably according to Regulation EC 440/2008 Part A.6, more preferably by the flask method of Regulation EC 440/2008 Part A.6.

The present invention further provides a process for preparing the crosslinked aminosiloxanes of the invention.

The present invention additionally provides compositions which comprise the crosslinked aminosiloxanes of the invention and/or the products of the process of the invention.

The present invention further provides formulations comprising the compositions of the invention, the formulations preferably being emulsifier-free.

In the context of the present invention, the crosslinked aminosiloxanes of the invention that are obtained by reaction of aminosiloxanes with epoxy polyethers are also referred to as hydrophilizing agents.

Dimensional stability is understood in the context of the invention to mean that, while the hydrophilizing agents do soften the fibers, they do not result in the fiber assembly exhibiting significant yielding under mechanical load, with the fibers sliding past one another, and with dimples or other deformations developing in the fabric. The fiber assembly preferably remains stable under the test conditions of ISO 13936, as described in more detail in the examples. More preferably, the fiber assembly is not pulled apart by more than 5% of its length. More preferably still, the fiber assembly is not pulled apart at the seam as per ISO 13936, on average, over the length of the seam, by more than 1 cm, more preferably more than 5 mm and more particularly more than 3 mm.

Another advantage of the crosslinked aminosiloxanes of the invention is that they form microemulsions in water without addition of an emulsifier.

Microemulsions in the context of the invention are aqueous mixtures of such crosslinked aminosiloxanes, which are really not water-soluble, having a droplet size of less than 200 nm, preferably less than 100 nm. As a result of the fine division, these mixtures appear clear or opalescent. In each case, the microemulsion is stable without change at 22° C. for at least 14 days, preferably for 6 months.

Emulsifier-free in the context of the invention means that the compositions and/or formulations of the invention contain no surface-active substances having more than eight carbon atoms. Ruled out accordingly are emulsifiers such as, for example, the fatty alcohol ethoxylates which are available commercially under the brand names Genapol® (trade mark of Clariant, Germany) Tego® Alkanol (trade mark of Evonik, Germany), or Lutensol® (trade mark of BASF, Germany). Likewise ruled out are emulsifiers such as alcoxylated isotridecanol containing 3 to 15 oxyalkylene units, and lauryl ethoxylates, including lauryl ethoxylates of technical lauryl alcohol, consisting optionally of a mixture containing $C_{12}$ and $C_{14}$ alkanol.

The crosslinked aminosiloxanes of the invention, the compositions of the invention comprising the crosslinked aminosiloxanes of the invention, and the inventive use of the crosslinked aminosiloxanes and of their compositions, and, additionally, the process of the invention for preparing the crosslinked aminosiloxanes, are described on an exemplary basis below, without any intention that the invention should be confined to these exemplary embodiments. References below to ranges, general formulae or classes of compound should be taken to encompass not only the corresponding ranges or groups of compounds that are explicitly mentioned, but also all sub-ranges and sub-groups of compounds that may be obtained by extracting individual values (ranges) or compounds. Where documents are cited in the context of the present description, it is intended that their content fully form part of the disclosure content of the present invention. Where % figures are given below, they are figures % by weight unless otherwise indicated. In the case of compositions, the % figures, unless otherwise indicated, are based on the overall composition. Where average values are reported below, the averages in question are mass averages (weight averages), unless otherwise indicated. Where measurement values are reported below, these measurement values, unless otherwise indicated, have been ascertained under a pressure of 101325 Pa and at a temperature of 25° C.

Aminosiloxane:

Preferred amino-substituted siloxanes with which the crosslinked aminosiloxanes of the invention are obtainable are those of the formula (I)

$$M_a M^A_b D_c D^A_d T_e T^A_f Q_g \quad (I)$$

$M = [R^1{}_3 SiO_{1/2}]$
$M^A = [R^2 R^1{}_2 SiO_{1/2}]$
$D = [R^1{}_2 SiO_{2/2}]$
$D^A = [R^2 R^1 SiO_{2/2}]$
$T = [R^1 SiO_{3/2}]$
$T^A = [R^2 SiO_{3/2}]$
$Q = [SiO_{4/2}]$, where
$R^1$ independently at each occurrence is identical or different, linear or branched, saturated or unsaturated hydrocarbon radicals having 1 to 30 carbon atoms or else aromatic hydrocarbon radicals having 6 to 30 carbon atoms, preferably methyl or phenyl, more particularly methyl;
$R^2$ independently at each occurrence is a hydrocarbon radical which is substituted by at least one nitrogen atom and has 1 to 30 carbon atoms,
a=0 to 20, preferably 1 to 10, more particularly 2;
b=0 to 10, preferably 0 to 5, more particularly 0;
c=10 to 5000, preferably 20 to 2000, more preferably 40 to 500, more particularly 80 to 250;
d=0 to 50, preferably greater than 0 to 40, more particularly 1 to 25;
e=0 to 20, preferably 0 to 10, more particularly 0;
f=0 to 500, preferably greater than 0 to 40, more particularly 1-25;
g=0 to 20, preferably 0 to 10, more particularly 0.

Preferably the sum of the indices a+b+c+d+e+f is at least 40, preferably at least 60, 80, more particularly at least 100. The upper limit of the sum of a+b+c+d+e+f is 10 000, preferably 5000, 3000, 1000, 500, 300 and more particularly 200.

The radical $R^2$ in formula (I) independently at each occurrence is preferably a hydrocarbon radical substituted by at least one primary amino group. The hydrocarbon radical is preferably an alkylene radical having 1 to 30 carbons, more preferably 2 to 15, more preferably more than 2 up to 10 carbons, optionally interrupted by heteroatoms selected from nitrogen, oxygen and/or sulphur, preferably interrupted by nitrogen atoms. In particular the alkylene radical is selected from ethylene, propylene, isopropylene, butylene, isobutylene, more preferably propylene. With particular preference, accordingly, the radical $R^2$ is a —$CH_2$—$CH_2$—$CH_2$—$NH_2$ radical.

More preferred amino-substituted siloxanes are substituted exclusively pendantly by $R^2$; even more preferred are linear amino-substituted siloxanes substituted pendantly by $R^2$; with particular preference the indices of the formula (I) are a=2 and b=e=f=g=0, c+d greater than 10, and especially preferably the indices of the formula (I) are a=2 and b=e=f=g=0, c+d greater than 10, and the radical $R^2$ is —$CH_2$—$CH_2$—$CH_2$—$NH_2$.

The weight-average molar mass Mw of the amino-substituted siloxanes is preferably between 1000 and 100 000 g/mol, more particularly 5000 and 60 000 g/mol.

The nitrogen content of the amino-substituted siloxanes is preferably between 0.1 and 2.0 wt %, preferably 0.2 and 1.2 wt %, more particularly 0.3 and 1.0 wt %. The nitrogen content is preferably determined in accordance with DIN 53176 as described in the examples.

Very preferred are amino-substituted siloxanes of the formula (I) having the indices a=2 and b=e=f=g=0, radical $R^2$ being —$CH_2$—$CH_2$—$CH_2$—$NH_2$, weight-average molar mass Mw being between 1000 and 60 000 g/mol, and the nitrogen content being from 0.2 to 1.2 wt %, based on the weight-average molar mass Mw.

Especially preferred are amino-substituted siloxanes of the formula (I) having the indices a=2 and b=b=e=f=g=0, radical $R^2$ being —$CH_2$—$CH_2$—$CH_2$—$NH_2$, weight-average molar mass Mw being between 1000 and 60 000 g/mol, and the nitrogen content being from 0.2 to 1.2 wt %, based on the weight-average molar mass Mw, the Mw being determined by means of GPC.

A further feature of the amino-substituted siloxanes is that the amount of D4 and D5 rings is less than 0.1 wt %, based on the sum of the amino-substituted siloxanes and of their process-related impurities. A further feature of the amino-substituted siloxanes is that even on storage with exclusion of atmosphere for at least 1 year, the amount of D4 and D5 rings is still below 0.1 wt %. Storage takes place preferably at 20° C.

The amino-substituted siloxanes can be prepared by methods of the prior art, but preferably by the process described in EP 12176057 (US 2013/0040875).

Epoxide Component:

Preferred epoxide components with which the crosslinked aminosiloxanes of the invention are obtainable are water-soluble hydrocarbons, the hydrocarbons comprising oxygen as well as carbon, the hydrocarbon having at least one chain which in turn has at least two oxygen atoms separated by at least one carbon atom, preferably by at least two carbon atoms, and the hydrocarbon having on numerical average more than one terminal epoxy group, preferably 2 terminal epoxy groups.

More preferably the epoxide components, as well as ether functions, have hydroxyl functions as well; more preferably the hydrocarbons are polyglycerols, carbohydrates or hydrocarbohydrates such as, for example, xylitol, sorbitol, mannitol, which on numerical average have more than one terminal epoxy group, preferably 2 terminal epoxy groups.

More preferably the epoxide components are water-soluble, terminally epoxy-substituted polyethers. Polyethers in the context of the invention are hydrocarbons which have a chain containing at least one section consisting of at least one alkylene group and of oxygen atoms alternating with the alkylene groups, the alkylene groups preferably being ethylene groups, which may optionally be substituted by hydrocarbon radicals consisting of carbon, hydrogen, oxygen and/or nitrogen, the hydrocarbon radical having a molar mass of not more than 500 g/mol, preferably not more than 200 g/mol.

More preferred are the epoxy-substituted polyethers of the formula (II)

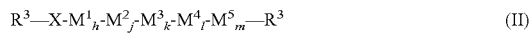

(II)

h=greater than 0 to 50, preferably 1 to 30, more preferably 2 to 25, more preferably still 3 to 20, more particularly 4 to 15;

j=0 to 10, preferably 0 to 5, more particularly greater than 0 to 2;

k=0 to 10, preferably 0 to 5, more particularly 0;

l=greater than 1 to 10, preferably 2 to 5, more particularly 2;

m=0 to 10, preferably 0 to 5, more particularly 0;

where the sum of the indices h, j, k, l+m is at least 3, preferably at least 5 and especially preferably at least 7, X=oxygen, $R^3$=independently at each occurrence hydrogen, a hydrocarbon having 1 to 8 carbon atoms and/or the glycidyl radical

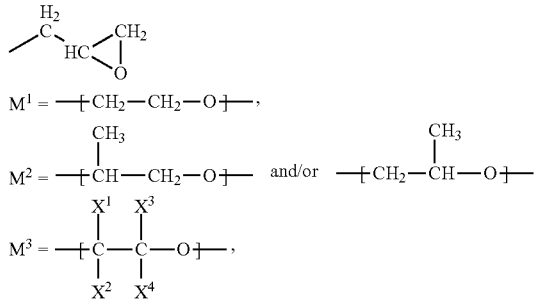

where in $M^3$, the radicals $X^1$ to $X^4$ independently of one another are hydrogen or linear, cyclic or branched, aliphatic or aromatic, saturated or unsaturated hydrocarbon radicals having 1 up to 50 C atoms, preferably 2 to 20 C atoms, and may optionally contain halogen atoms, with the proviso that $X^1$ to $X^4$ are not selected such that $M^3$ is the same as $M^1$ or $M^2$,

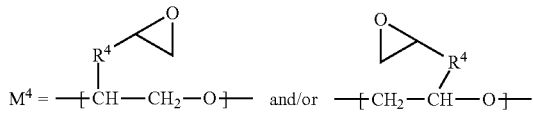

where $R^4$ in $M^4$ independently at each occurrence is a hydrocarbon radical having 2 to 20 carbons, and may be interrupted by heteroatoms, preferably $M^4$ is a glycidyl ether=

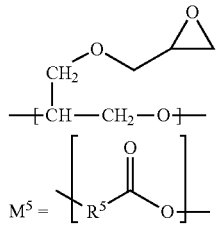

where $R^5$ in $M^5$ independently at each occurrence is not present or is a divalent hydrocarbon having 1 to 10 carbon atoms, preferably more than 1 up to 6, more particularly 2 up to 4 carbon atoms.

The hydrocarbon in $R^3$ is preferably an alkyl radical or a carboxylic acid radical. The alkyl radical is preferably a methyl, ethyl or propyl radical. The carboxylic acid radical is preferably an acetyl, propionyl, butyryl, valeryl or caproyl radical, especially preferably an acetyl radical.

More preferably the radical $R^5$ in $M^5$ is an alkylene radical, very preferably a methylene radical.

The epoxy-substituted polyethers of the formula (II) preferably have a molar mass of 200 to 1500 g/mol, more preferably of 250 to 1000 g/mol and more particularly of 300 to 600 g/mol.

The molar mass is preferably calculated in accordance with formula (II) or determined by means of GPC, being more particularly determined by means of GPC.

The epoxy-substituted polyethers of formula (II) preferably have a polydispersity of less than 2, more preferably of less than 1.8, especially preferably of less than 1.5, the polydispersity being determined by means of GPC.

The epoxy-substituted polyethers of the formula (II) preferably have a viscosity of 10 to 10 000 mPa*s at 20° C., the viscosity being determined preferably by means of a rheometer at 25° C., using a plate/plate configuration, more particularly as described in the examples.

The epoxy-substituted polyethers of the formula (II) are preferably colorless.

For the indices in the epoxy-substituted polyethers of the formula (II), j, k, l and m are preferably 0, and h is preferably greater than zero. With more particular preference, the epoxy-substituted polyethers are polyethylene glycols which have undergone terminal reaction with epichlorohydrin. They preferably therefore have a radical $R^3$ which is

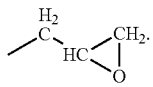

More preferably the epoxy-substituted polyethers of the formula (II) are colorless and have a polydispersity of less than 1.5. Especially preferred are the epoxy-substituted polyethers of the formula (II) having indices h of more than 3 and j, k, l and m of zero and $R^3$ of the radical

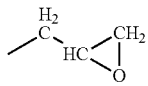

are colorless and have a polydispersity of less than 1.5.

The reaction forming the crosslinked aminosiloxanes of the invention is an addition reaction, in which the molar mass of the product is calculated by adding the molar masses of the amino-substituted siloxanes and of the epoxide component.

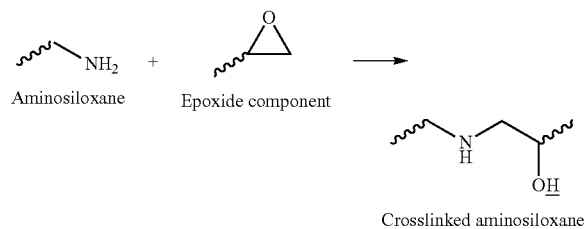

Aminosiloxane    Epoxide component

Crosslinked aminosiloxane

In all molar mass considerations of this reaction, the hydrogen shown with underlining in the reaction scheme is still counted as belonging to the amino-substituted siloxane.

The crosslinked aminosiloxanes of the invention have preferably less than 10 wt %, preferably less than 6 wt % and more particularly less than 4 wt %, but at least 0.01 wt %, polyether fraction.

In the crosslinked aminosiloxanes, preferably at least 50%, more preferably at least 60%, at least 70%, at least 75% and more particularly at least 80% of the primary amino groups of the aminosiloxane have not undergone reaction by crosslinking with epoxide groups.

With further preference, the crosslinked aminosiloxanes of the invention have a weight-average molar mass Mw which is 1.2 to 15 times higher, preferably 1.5 to 5 times higher, than the weight-average molar mass Mw of the amino-substituted siloxanes prior to crosslinking.

The weight-average molar mass Mw can be determined by various methods of the prior art, and is determined preferably by means of GPC; with more particular preference, the weight-average molar mass Mw is determined by the method specified in the examples, more particularly using the corresponding calibration standards.

Particularly preferred are crosslinked aminosiloxanes of the invention which have a weight-average molar mass Mw 1.5 to 5 times higher than the weight-average molar mass Mw of the amino-substituted siloxanes prior to crosslinking, and in which at least 80% of the primary amino groups of the crosslinked aminosiloxane have not undergone reaction by crosslinking with epoxide groups.

More particularly preferred are crosslinked aminosiloxanes of the invention which have less than 4 wt % polyether fraction and in which at least 80% of the primary amino groups of the aminosiloxane have not undergone reaction by crosslinking with epoxide groups, and where the weight-average molar mass Mw is 1.5 to 5 times higher than the weight-average molar mass Mw of the amino-substituted siloxanes prior to crosslinking.

The individual fragments of the formulae (I) and (II) may preferably be of statistical construction.

Statistical distributions are of blockwise construction with any desired number of blocks and with any desired sequence or subject to a randomized distribution; they may also have an alternating construction or else form a gradient over the chain; more particularly they can also form all hybrid forms in which optionally groups with different distributions may follow one another. Specific embodiments may result in limitations on the statistical distributions as a result of the embodiment. For all ranges which are not affected by the restriction, there is no change in the statistical distribution.

The crosslinked aminosiloxanes of the invention can be prepared by the methods of the general prior art, but the process of the invention described hereinafter is preferred.

A feature of the process of the invention for preparing the crosslinked aminosiloxanes of the invention is reaction of amino-substituted siloxanes with epoxide components in an organic solvent over the course of several hours at a temperature elevated relative to room temperature.

The reaction may take place with the catalysts known in the prior art, or else in the absence of catalysts. The reaction is carried out preferably without catalyst, solely in the presence of solvent. After the epoxide groups have been consumed by reaction, the solvent is removed by distillation, unless it is able to remain in the product as part of the formulation.

The amount of solvent is preferably from 5 to 50 wt %, more preferably from 15 to 40 wt %, more preferably still from 20 to 30 wt % of the sum total of the initial masses of amino-substituted siloxane, epoxide component and solvent.

Preferred organic solvents are protic solvents, more particularly mono- or dihydroxy compounds of the alkanes with a boiling point of below 150° C., selected more preferably from methanol, ethanol, propanol, isopropanol, butanol, isobutanol, pentanol and hexanol, glycol ethers, diglycol ethers, propylene glycol, dipropylene glycol, propylene glycol ethers, dipropylene glycol ethers; more preferably still, organic solvents are monohydroxyalkanes having a boiling point below 120° C., more preferably selected from methanol, ethanol, propanol, isopropanol, butanol, isobutanol, pentanol and hexanol, especially preferably isopropanol.

Preferred temperatures of the process of the invention are 40 to 140° C., preferably 50 to 110° C., more preferably 60 to 90° C. The process of the invention is carried out preferably with a reaction time of 2 to 12 hours, more preferably with 2.5 to 10 hours and very preferably with 3 to 8 hours.

The epoxide components are preferably in a stoichiometric deficit relative to the amino-substituted siloxanes. This deficit relates to the number of epoxy groups in the water-soluble, terminally epoxy-substituted compounds in relation to the amino groups in the siloxane. More preferably the molar ratio of the epoxy groups of the epoxide component to the amino groups of the amino-substituted siloxanes is <=50:50, more preferably <=40:60, very preferably <=30:70, more preferably still <=25:75, especially preferably <=20:80 but not less than 0.1:99.9.

The process of the invention for preparing the crosslinked aminosiloxanes of the invention is notable with particular preference for the fact that an amino-substituted siloxane is admixed with 20 wt % of a solvent and with the epoxide component. The quantity figures in wt % relate to the sum of the initial masses of aminosiloxane, solvent and epoxide component. The sum adds up to 100 wt %. Preferably the reaction mixture is stirred and heated to a temperature in the preferred range of 70 to 90° C. and stirred for further 4 to 8 h at that temperature. Following removal of the solvent by distillation at 70 to 90° C. under a reduced pressure of 1 to 25 mbar, preferably of 10 to 20 mbar, the crosslinked aminopropylsiloxanes of the invention are obtained.

A feature of the compositions of the invention comprising the crosslinked aminosiloxanes of the invention or the products of the process of the invention is that they comprise 0.1 wt %, preferably at least 0.3 wt %, more preferably at least 0.5 wt %, more particularly at least 1 wt %, based on the mass of the crosslinked aminosiloxanes, of an acid. The maximum amount of the acid is preferably not more than 5 wt %, more preferably not more than 4 wt %, 3 wt %, and more particularly not more than 2 wt %.

The acids are preferably inorganic or organic acids or mixtures of these, both inorganic and organic, and also in the two groups with one another. More preferred are organic acids or mixtures thereof with one another.

The organic acid is preferably an organic acid having a boiling point above 100° C. under standard conditions, more preferably above 120° C. With further preference the organic acid has a melting point of above 0° C., preferably above 20° C., more preferably above 50° C.; in the case of chiral organic acids, the melting point refers to the enantiomerically pure substances. More preferably the organic acids have a pKa of 3.5 to 5.0, more preferably still of 3.8 to 4.8. With particular preference the organic acids are selected from acetic acid, glycolic acid, and lactic acid. With more particular preference the organic acids, as well as a carboxylate group, also have a hydroxyl group; with more particular preference still, the organic acids, as well as a carboxylate group, contain no nitrogen. In particular the acids are selected from glycolic and/or lactic acid with preference.

The inorganic acids are preferably hydrochloric acid, sulphuric acid or phosphoric acid.

Preferred compositions of the invention have 0.5 to 3 wt %, preferably 1 to 2 wt %, of an acid selected from acetic acid, glycolic acid and lactic acid. More preferred compositions of the invention have 0.5 to 3 wt %, preferably 1 to 2 wt %, of an acid mixture selected from the organic acids acetic acid, glycolic acid and lactic acid together with the inorganic acid phosphoric acid.

A feature of the formulations of the invention is that as well as the compositions of the invention they comprise a viscosity regulator.

The viscosity regulator is preferably a hydrocarbon containing up to 8 carbon atoms. More preferably the viscosity regulator also contains oxygen. With particular preference, the viscosity regulator comprises functional groups which are ether groups and at least one hydroxyl group. With more particular preference the viscosity regulator, as well as the ether groups, contains only one terminal hydroxyl group and no other heteroatoms. With very particular preference, the viscosity regulator is diethylene glycol monobutyl ether (BDG).

The formulations of the invention preferably further comprise water, more preferably at least 30 wt %, more preferably still at least 50 wt %, 60 wt %, 70 wt %, 80 wt %, very preferably at least 90 wt %, and especially preferably at least 95 wt %, based on the total mass of the formulation.

Especially preferred are formulations of the invention for storage that comprise 5 to 30 wt % of crosslinked aminosiloxane, 2 to 25 wt % of BDG, 0.05 to 1 wt % of an organic acid and 50 to 95 wt % of water, with all of the wt % figures being based on the sum total mass of this formulation.

The formulations are preferably stored at temperatures of 23° C.

An advantage of the formulations of the invention is that they are further water-dilutable, in other words that further water can be added, without further addition of any of the other components, without phase separation occurring. As a result of this dilution, the formulation for use is obtained.

Another advantage is that it is not necessary to add further acid.

A further advantage is that the crosslinked aminosiloxanes of the invention, in spite of their high silicone character, can be formulated in emulsifier-free form; emulsifier-free has already been defined above.

The formulations for use are prepared from the formulations for storage by dilution with water, preferably mains water having a low to medium hardness (7-12° dH [German hardness]). Preferred dilution ratios are 1-10 g/l, depending on further processing. Particularly preferred are about 4 g/l of the 20% concentrate (0.08% active substance of the compound according to the invention).

The formulations are preferably diluted in temperatures of 23° C.

A disadvantage of the nonionic surfactants used in the prior art, such as fatty alcohol ethoxylates, is that their long-chain alkyl radical adsorbs on to the textile fabric and thus blocks part of the surface, which is then not wetted with aminosiloxane. After the nonionic surfactants have been washed off, the surface that is uncovered again has the properties of the untreated fabric. This effect dilutes the efficiency of the softening aminosiloxanes.

A further advantage of the crosslinked aminosiloxanes of the invention is that the small amounts of the epoxide component as crosslinker are sufficient to bring about ease of formulation in aqueous systems and good technical performance in textile finishing.

A further advantage of the composition of the invention is therefore a higher efficiency in the softening effect.

A disadvantage of the aminosiloxanes used in the prior art is that at typical finishing temperatures of 100° C. or more there is phase separation, and the droplets formed in that process lead to spotting in application on textiles. As a result of the locally increased concentrations, the aminosiloxanes can react with themselves and possibly lead to instances of sticking on the dyeing machines. This might in particular affect exhaust process machines, such as beam dyeing apparatus, jiggers, jet dyeing machines, winch becks, etc., causing unwanted deposits.

A further advantage is the outstanding storage stability of the formulations of the invention. Hence the formulations are distinguished by high color stability—that is, they continue to be colorless even after storage at 25° C. for 4 weeks. Another feature thereof is that the emulsions in the formulations show no signs of phase separation even after prolonged storage, i.e. after 4 weeks or longer at 25° C.

A further advantage of the softener use in accordance with the invention is that the softener endows the fabrics treated therewith with hydrophilic qualities.

In particular, the crosslinked aminosiloxanes of the invention endow the fabrics with hydrophilic qualities while at the same time producing a good soft hand.

Likewise provided by the invention is the use of the crosslinked aminosiloxanes of the invention and also of the process products of the invention in household products, preferably as fabric softeners and hair conditioners.

When textiles are treated with the compositions of the invention, then, a good soft hand with high permanence is obtained, in other words an enhancement of the textile that is retained after laundering. In particular, and in spite of softer, slippier fibers, the dimensional stability of the fabric is retained in the textile, thereby ensuring the high-grade nature of the garment for the customer.

One preferred use of the crosslinked aminosiloxanes of the invention is as softeners for fabrics. Preferred fabrics are selected, for example, from the group encompassing woven fabrics, textile wovens, knits, crocheted fabrics, non-wovens, tissues (paper fibers) and/or fibers of natural and/or synthetic raw materials and/or leather and/or hair and/or fur. The materials preferably comprise polyesters and polyamides; more preferably, the textiles comprise polyesters, and with particular preference the textiles are made from polyester.

The crosslinked aminosiloxanes of the invention or compositions and formulations of the invention are used preferably for the OEM finishing of textiles.

With further preference, the crosslinked aminosiloxanes of the invention are used as textile care agents and/or as hydrophilizing agents for textiles.

BRIEF DESCRIPTION OF THE FIGURES

FIG. 1: Schematic representation of elongation in accordance with ISO 13936. The line in the middle is the seam; the direction of tension is vertical.

EXAMPLES

General Methods and Materials
Spectroscopic Analyses:

The chain length of the crosslinked aminosiloxanes and of the amino-substituted siloxanes was determined using $^{29}$Si NMR. The recording and interpretation of NMR spectra is known to the skilled person. References include the book "NMR Spectra of Polymers and Polymer Additives", A. Brandolini and D. Hills, 2000, Marcel Dekker, Inc. The spectra were recorded at room temperature with a Bruker Spectrospin spectrometer, with measurement frequencies when recording the proton spectra of 399.9 MHz, when recording the $^{13}$C spectra of 100.6 MHz and when recording the $^{29}$Si spectra of 79.5 MHz.

Determination of molar masses, in particular the weight-average molar masses Mw: The gel permeation chromatographic analyses (GPC) were performed with a type 1100 instrument from Hewlett-Packard using an SDV column combination (1000/10000 Å, each 65 cm, internal diameter 0.8 cm, temperature 30° C.), THF as mobile phase with a flow rate of 1 ml/min and an RI detector (Hewlett-Packard). The system was calibrated against a polystyrene standard in the range from 162 to 2 520 000 g/mol for the determination of the molar masses of the crosslinked aminosiloxanes and of the amino-substituted siloxanes, and against a polypropylene glycol standard in the range from 162 to 2 520 000 g/mol for determining the molar masses of the epoxide components.

The nitrogen content is determined by potentiometric titration in a method based on DIN EN ISO 9702. The total nitrogen was determined as per 2.1.1, and the sum total of secondary and tertiary nitrogen was determined as per 2.2.3, and the primary nitrogen was calculated from these results by formulation of the difference. The aprotic solvent used was dioxane, and the acid was perchloric acid.

The viscosity is determined using a rotary viscometer according to DIN 53018 Part 1 in a plate/plate method. An ES-CPS-Plus rheometer from Brookfield was used, with the RP 75 measuring plate, gap width 1 mm. The measurements were conducted at 25° C.

Example 1

Synthesis 1.1: Preparation of Amino-Substituted Siloxanes in Accordance with DE 102011110100 A1

The preparation of amino-substituted siloxanes was carried out in accordance with DE 102011110100. The amounts of each of the raw materials used are derived directly from the stoichiometry of the polymer composition. Figures in wt % are always based on the sum total of all the initial masses.

In a four-necked round-bottomed flask equipped with stirrer, internal thermometer and distillation bridge, dihydroxy-functional polydimethylsiloxane with known chain length, determined by $^{29}$Si NMR, hexamethyldisilazane and 0.07 wt % of an 85 percent strength by weight phosphoric acid are heated with stirring for 85° C. and stirred at that temperature for 30 minutes. Then aminopropylmethyl diethoxysilane and a further 0.07 wt % of an 85 percent strength by weight phosphoric acid are added, and the mixture is distilled at 85° C. at 14 to 20 mbar for an hour, and also at 120° C. for a further 2 hours. Filtration through a pressure filter press produces transparent, colorless aminopropylsiloxanes. Examples are reported in Table 1.

TABLE 1

Aminopropylsiloxanes of Example 1.1; the chain length relates to the number of siloxane units

| Aminopropylsiloxane | Chain length | Nitrogen, [wt %] | Mw [g/mol] |
|---|---|---|---|
| AS1 | 81 | 0.32 | 12628 |
| AS2 | 210 | 0.76 | 35665 |
| AS3 | 246 | 0.73 | 45462 |
| AS4 | 202 | 0.98 | 40090 |
| AS5 | 75 | 0.98 | 11147 |

TABLE 1-continued

Aminopropylsiloxanes of Example 1.1; the chain length relates to the number of siloxane units

| Aminopropylsiloxane | Chain length | Nitrogen, [wt %] | Mw [g/mol] |
|---|---|---|---|
| AS6 | 68 | 1.00 | 11818 |
| AS7 | 75 | 0.32 | 12618 |
| AS8 | 216 | 0.93 | 45710 |
| AS9, not inventive | 277 | 0.39 | 36163 |

1.2: Preparation of Inventive Crosslinked Aminosiloxanes

An aminopropylsiloxane is charged to a four-necked round-bottomed flask equipped with stirrer, internal thermometer and distillation bridge and is admixed with 20 wt % of 2-propanol and also with the epoxide component in the amount required in each case according to Table 2. The quantity figures in wt % relate to the sum total of the initial masses of aminosiloxane, solvent and epoxide component. The sum total makes up 100 wt %.

The charge is heated to 80° C. with stirring and is stirred at this temperature for 6 hours. Following removal of the solvent by distillation at 80° C. under a reduced pressure of <20 mbar, the crosslinked aminopropylsiloxanes are obtained. Examples are set out in Table 2.

TABLE 2

Crosslinked aminopropylsiloxanes of Example 1.2

| Crosslinked aminosiloxane | Amino-substituted siloxane | Epoxide component 1 * [wt %] | Nitrogen primary | [wt %] tertiary | Mw [g/mol] |
|---|---|---|---|---|---|
| HS1 | AS3 | 0.67 | 0.72 | | 108776 |
| HS2 | AS5 | 3.22 | n.d. | | 144311 |
| HS3 | AS1 | 1.07 | 0.29 | 0.02 | 17463 |
| HS4 | AS6 | 0.68 | 0.99 | | 50264 |
| HS5 | AS7 | 2.61 | 0.28 | 0.04 | 31289 |
| HS6 | AS8 | 0.87 | 0.88 | | 244066 |
| HS7 | AS8 | 0.44 | 0.89 | | 86860 |
| HS8 | AS9 | 1.2 | 0.38 | 0.01 | 76978 |

* The epoxy component 1 was a diepoxyfunctional polyethyleneglycol according to formula (II), having indices h of 10 and j, k, l and m of zero and $R^3$ of the glycidyl radical

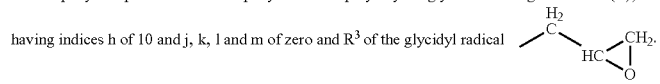

From the values reported it is apparent that at least 80% of the primary amino groups were still present unchanged after the reaction with the epoxy compound.

Example 2

Compositions and Formulations

Typical compositions of the invention contain 20 wt % of crosslinked aminosiloxane, 15 wt % of diethylene glycol monobutyl ether (BDG), 0.3 wt % of an organic acid and 64.7 wt % of water.

The compositions are prepared by simple stirring together at room temperature. Stirring is continued until the mixture is a homogeneous single-phase mixture, i.e. has no visible second phase. In general the formulations are homogeneous within 10 minutes of stirring. Depending on the viscosity of the crosslinked aminosiloxane, a KPG stirrer is used, or a magnetic stirrer is sufficient. The compositions of the invention are clear, transparent or else milkily turbid.

They remain homogeneous after the stirrer is shut off, and exhibit neither phase separation nor yellowing even on two-week storage at 22° C.

In a formulation of this kind, non-inventive aminosiloxanes, not hydrophilized by crosslinking, exhibit rapid phase separation since they lack the emulsifier.

TABLE 3

Formulations of Table 2 of the crosslinked aminosiloxanes of Example 1.2, all containing 15 wt % BDG and 64.7 wt % water

| Formulation | Crosslinked aminosiloxane [wt %] | Acid [wt %] | Appearance |
|---|---|---|---|
| | | acetic acid | |
| FHS1 | 20 (HS1) | 0.3 | clear, homogeneous, colorless |
| FHS2 | 20 (HS2) | 0.3 | turbid, homogeneous, colorless |
| FHS3 | 20 (HS3) | 0.3 | turbid, homogeneous, colorless |
| FHS4 | 20 (HS4) | 0.3 | turbid, homogeneous, colorless |
| FHS5 | 20 (HS5) | 0.3 | slightly turbid, homogeneous, colorless |
| FHS6 | 20 (HS6) | 0.3 | clear, homogeneous, colorless |
| FHS7 | 20 (HS7) | 0.3 | clear, homogeneous, colorless |
| FHS8 | 20 (HS8) | 0.3 | turbid, homogeneous, colorless |
| | | lactic acid | |
| FHS9* | 20 (HS1) | 0.3 | clear, homogeneous, colorless |
| | | glycolic acid | |
| FHS10 | 20 (HS1) | 0.3 | clear, homogeneous, colorless |

*FHS9 was prepared by stirring at 50° C.

The formulations were tested for their dilutability with water, by the addition to 1 g of the formulation of 6 g of water, followed by brief stirring together with a magnetic stirrer. The appearance was tested for homogeneity, and remains comparable in all cases with the appearance of the concentrated formulation from Table 3.

TABLE 4

Water-dilutability of the formulations from Table 3

| Starting formulation | Appearance |
|---|---|
| FHS1 | clear, homogeneous, colorless |
| FHS2 | turbid, homogeneous, colorless |
| FHS4 | turbid, homogeneous, colorless |
| FHS5 | slightly turbid, homogeneous, colorless |
| FHS6 | clear, homogeneous, colorless |
| FHS7 | clear, homogeneous, colorless |
| FHS8 | slightly turbid, homogeneous, colorless |

Phase separation was not observed for any of the formulations of Example 2.

Example 3

Application Tests

Pretreatment of the Test Fabric:

The standard fabric is first of all pretreated. It is washed initially once with 32 g of test detergent, and then once without test detergent.

The washing operations took place in a commercial Miele Novotronic W 918 washing machine with colored laundry, without prewashing at 40° C., using wfk standard laundry detergent IECA-Base and 3 kg of cotton ballast fabric. Lastly, the fabric thus treated was dried at room temperature for 12 hours. The test fabrics are cut into pieces measuring 30×40 cm.

A1:

For the testing, polyester fabrics from wfk Testgewebe GmbH (Christenfeld 10 41379 Brüggen) with wfk code 30A, basis weight 170 g/m², woven goods with 1/1 weave and three dyed taffetas (woven polyester goods with 1/1 weave) with different basis weights were used, and were immersed at 25° C. in a 0.08% (based on active substance) liquor with a liquor-to-goods ratio of 12 to 1 for 20 minutes with gentle mixing, after which they were wrung out gently and dried in a Matthis Labdryer LTE. The drying conditions were 2 minutes at 105° C. followed by 1 minute at 180° C.

Compositions FHS1 to FHS8 were diluted with cold mains water to form a rinsing solution which contains 0.08 wt % of inventive compound.

Comparative samples were conducted using alternative softeners, a non-crosslinked amino silicone AS9 (Table 1) (Comparative 2) and a linearly polymerized ABn silicone (Momentive SRS, molar mass about 50 000 g/mol) (Comparative 1) in the same way as for the inventive experiments.

V1, Soft Hand:

To assess the soft hand, an experienced team of eight individual testers was assembled, who used a hand panel test to evaluate the anonymized hand specimens of the polyester fabrics finished using the formulations. In this test, each tester receives their own cloth. For the hand specimens, additionally, an untreated sample without obvious marking (blank value) was always added on.

Assessment took place on a scale from 0 (hard and unpleasant to handle) to 5 (soft and pleasant to handle) with the possibility of whole-number values in between. For the assessment of the soft hand, the individual evaluations were added up, meaning that, with 8 testers, a maximum soft hand value of 40 was possible. The results are listed in Table #5. Not all of the compositions were tested.

TABLE #5

Soft hand assessment of Example 3 after application A1 of the compositions of Example 2 to knitted polyester goods

| | Soft hand/material | | | |
|---|---|---|---|---|
| Composition | PES black 210 g/m² | PES blue 170 g/m² | PES red 170 g/m² | PES Wfk |
| FHS 1 | 20.5 | 12 | 17 | 32 |
| FHS 2 | 23 | | | 29 |
| FHS 3 | 35 | | | 37 |
| FHS 4 | | 17 | 30.5 | 29 |
| FHS 5 | | | | 24 |
| FHS 7 | 26 | 21 | 18.5 | 24 |
| FHS 8 | | 28 | 14.5 | 37 |
| Comparative 1 | 20 | 28 | 24 | 32 |
| Comparative 2 | 19 | 21 | 26.5 | 29 |

The inventive compositions are comparable with the prior art.

V2: Deformation

Tensile tests with samples of woven fabric (A1) were carried out according to ISO 13936. The material used was exclusively taffeta. The tensile tests were carried out in the direction of the warp threads. In the diagrams, the warp threads run vertically. Samples were pretreated according to A1 and then two pieces were stitched together with the test thread.

The seam width in the tensile test of the untreated sample is on average 2 mm across the entire breadth, with an applied force of 120 N. The average values after application of the inventive compositions are reported in Table #6.

TABLE #6

Tensile test according to V2, ISO 13936 Part 1, force at defined seam opening (weft thread):

| Formulation | Seam opening (weft) [mm] | Force [N] |
|---|---|---|
| untreated | 2 | 120 |
| FHS1 | 6 | 120 |
| FHS4 | 5 | 120 |
| FHS6 | 5 | 120 |
| FHS8 | 5 | 120 |
| Comparative 1 | 6 | 120 |
| Comparative 2 | 7 | 120 |

Table #7 shows the force values needed for a seam opening of 6 mm. Since the maximum force was 199 N, the value of the untreated sample shows only a seam opening of 2.9 mm.

TABLE #7

Tensile test according to V2, ISO 13936 Part 2, force at defined seam opening (weft thread):

| Formulation | Seam opening (weft) [mm] | Force [N] |
|---|---|---|
| untreated | 2.9 | 199 |
| FHS1 | 6 | 199 |
| FHS4 | 6 | 199 |
| FHS6 | 6 | 199 |
| FHS8 | 6 | 199 |
| Comparative 1 | 6 | 164 |
| Comparative 2 | 6 | 143 |

Advantageous values are a smaller seam opening for a given force and/or a greater force for a given seam opening. In both cases it is apparent that the deformation after inventive finishing was better than after application of the comparative compositions of the prior art.

V3: Heat Resistance:

Samples of Example 2 (Table 3) were adjusted at room temperature to a pH of between 4 and 4.5, with addition of acetic acid where necessary, and were stirred gently with a double-paddle stirrer. The temperature was raised to 100° C. for 30 minutes, after which the samples were cooled to room temperature. The stirrer was shut off and the sample was left to stand at rest for 10 minutes, after which it was inspected.

All inventive samples show no signs of phase separation, and in particular do not exhibit any droplet formation at the meniscus with the glass wall. The non-crosslinked amino silicone (corresponding to Comparative 2) exhibited droplet formation after treatment above.

The invention claimed is:

1. A crosslinked aminosiloxane obtained by reaction of identical or different amine-substituted siloxanes with identical or different epoxide components which are water-soluble hydrocarbons, the hydrocarbons comprising oxygen and carbon, the hydrocarbon having on average more than one terminal epoxy group, the epoxy group being a carbooxirane radical, and, further, not more than 50% of all the amino groups having undergone reaction with an epoxide group
   wherein the epoxide components are epoxy-substituted polyethers of formula (II)

$$R^3\text{---}X\text{-}M^1_h\text{-}M^2_j\text{-}M^3_k\text{-}M^4_l\text{-}M^5_m\text{-}R^3 \qquad (II)$$

h=greater than 0 to 50;
   j=0 to 10;
   k=0 to 10;
   l=greater than 1 to 10;
   m=0 to 10;
   where the sum of the indices h, j, k, l+m is at least 3,
   X=oxygen,
   $R^3$=independently at each occurrence hydrogen, a hydrocarbon having 1 to 8 carbon atoms, and/or the gycidyl radical

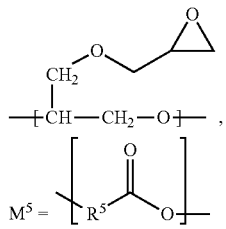

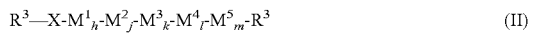

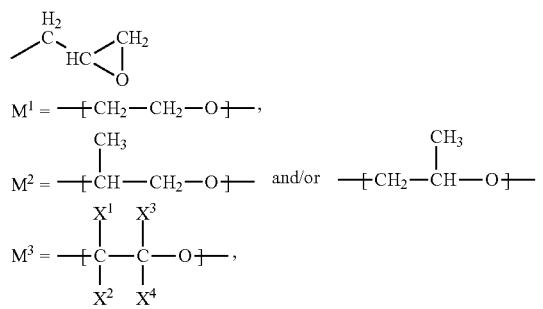

where in $M^3$, the radicals $X^1$ to $X^4$ independently of one another are hydrogen or linear, cyclic or branched, aliphatic or aromatic, saturated or unsaturated hydrocarbon radicals having 1 up to 50 C atoms, wherein $X^1$ to $X^4$ are not selected such that $M^3$ is the same as $M^1$ or $M^2$,

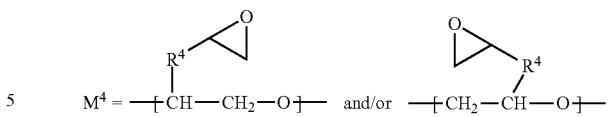

where $R^4$ in $M^4$ independently at each occurrence is a hydrocarbon radical having 2 to 20 carbons, and may be interrupted by heteroatoms, $M^4$ is a glycidyl ether=

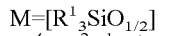

where $R^5$ in $M^5$ independently at each occurrence is not present or is a divalent hydrocarbon having 1 to 10 carbon atoms.

2. The crosslinked aminosiloxane according to claim 1, wherein the amine-substituted siloxanes conform to the formula (I)

$$M_a M^A_b D_c D^A_d T_e T^A_f Q_g \qquad (I)$$

where
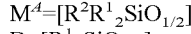
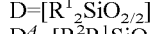
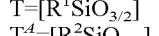
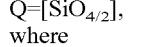
$Q=[SiO_{4/2}]$,
where
$R^1$ independently at each occurrence is identical or different, linear or branched, saturated or unsaturated hydrocarbon radicals having 1 to 30 carbon atoms or else aromatic hydrocarbon radicals having 6 to 30 carbon atoms,
$R^2$ independently at each occurrence is a hydrocarbon radical which is substituted by at least one nitrogen atom and has 1 to 30 carbon atoms,
a=0 to 20,
b=0 to 10,
c=10 to 5000,
d=0 to 50,
e=0 to 20,
f=0 to 500,
g=0 to 20.

3. The crosslinked aminosiloxane according to claim 1, wherein the epoxide components are water-soluble hydrocarbons, the hydrocarbons comprising oxygen as well as carbon, the hydrocarbon having at least one chain which in turn has at least two oxygen atoms separated by at least one carbon atom and the hydrocarbon having on numerical average more than one terminal epoxy group.

4. The crosslinked aminosiloxane according to claim 1, wherein the epoxy-substituted polyethers of the formula (II) have a molar mass of 200 to 1500 g/mol.

5. The crosslinked aminosiloxane according to claim 1, wherein the epoxy-substituted polyethers of formula (II) are colorless.

6. The crosslinked aminosiloxane according to claim 1, wherein the crosslinked aminosiloxanes have less than 10 wt %, but at least 0.01 wt %, polyether fraction.

7. The crosslinked aminosiloxane according to claim 1, wherein at least 50% of the primary amino groups of the crosslinked siloxanes have not undergone reaction by crosslinking with epoxide groups.

8. The process for preparing the crosslinked aminosiloxane according to claim 1.

9. A composition comprising the crosslinked aminosiloxane of claim 1.

10. The composition according to claim 9, wherein they comprise from 0.1 wt % to 5 wt %, based on the mass of the crosslinked aminosiloxane, of an acid.

11. A formulation comprising the composition according to claim 9, wherein the formulation is emulsifier-free.

12. A household product including fabric softener and hair conditioner wherein the household product comprised the crosslinked aminosiloxane of claim 1.

13. The crosslinked aminosiloxane according to claim 1 wherein the hydrocarbons may further consist of elements selected from the group consisting of nitrogen, sulphur and phosphorus.

14. The crosslinked aminosiloxane according to claim 1 wherein the epoxide components the hydrocarbon having at least one chain which in turn has at least two oxygen atoms separated by at least two carbon atoms, and the hydrocarbon having on numerical average more than two terminal epoxy groups.

15. The crosslinked aminosiloxane according to claim 1, wherein the epoxide components are epoxy-substituted polyethers of formula (II)

(II)
h=from 4 to 15;
j=0 to 5;
k=0;
l=from 2 to 5;
m=0;
where the sum of the indices h, j, k, l+m is at least 5,
X =oxygen,
$R^3$=independently at each occurrence hydrogen, a hydrocarbon having 1 to 8 carbon atoms and/or the gycidyl radical $$\mathrm{\underset{HC}{\overset{H_2}{C}}\underset{O}{\overset{CH_2}{\diagdown}}}$$

$M^1 = -\!\!\left[CH_2-CH_2-O\right]\!\!-,$ $M^2 = -\!\!\left[\underset{\underset{CH_3}{|}}{CH}-CH_2-O\right]\!\!-$ and/or $-\!\!\left[CH_2-\underset{\underset{CH_3}{|}}{CH}-O\right]\!\!-$ $M^3 = -\!\!\left[\underset{\underset{X^2}{|}}{\overset{\overset{X^1}{|}}{C}}-\underset{\underset{X^4}{|}}{\overset{\overset{X^3}{|}}{C}}-O\right]\!\!-,$ where in $M^3$, the radicals $X^1$ to $X^4$ independently of one another are hydrogen or linear, cyclic or branched, aliphatic or aromatic, saturated or unsaturated hydrocarbon radicals having 1 up to 50 C atoms, wherein $X^1$ to $X^4$ are not selected such that $M^3$ is the same as $M^1$ or $M^2$, $M^4 = -\!\!\left[\underset{\underset{R^4}{|}}{CH}-CH_2-O\right]\!\!-$ and/or $-\!\!\left[CH_2-\underset{\underset{R^4}{|}}{CH}-O\right]\!\!-$ where $R^4$ in $M^4$ independently at each occurrence is a hydrocarbon radical having 2 to 20 carbons, and may be interrupted by heteroatoms, $M^4$ is a glycidyl ether=

$$-\!\!\left[\underset{\underset{CH_2-O-CH_2-\triangle}{|}}{CH}-CH_2-O\right]\!\!-,$$

$M^5 = \left[R^5\overset{O}{\underset{}{\diagup\!\!\diagdown}}O\right]\!\!-$ where $R^5$ in $M^5$ independently at each occurrence is not present or is a divalent hydrocarbon having 1 to 10 carbon atoms.

16. The crosslinked aminosiloxane according to claim 2, wherein the epoxy-substituted polyethers of the formula (II) have a molar mass of 200 to 1500 g/mol.

* * * * *